(12) United States Patent
Mochizuki

(10) Patent No.: US 6,796,943 B2
(45) Date of Patent: Sep. 28, 2004

(54) ULTRASONIC MEDICAL SYSTEM

(75) Inventor: Takashi Mochizuki, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 0 days.

(21) Appl. No.: 10/397,788

(22) Filed: Mar. 26, 2003

(65) Prior Publication Data

US 2003/0187345 A1 Oct. 2, 2003

(30) Foreign Application Priority Data

Mar. 27, 2002 (JP) ........................................ 2002-088154
Mar. 7, 2003 (JP) ........................................ 2003-061120

(51) Int. Cl.[7] ................................................ A61B 8/00
(52) U.S. Cl. ...................................... 600/437; 600/429
(58) Field of Search ................................ 600/407, 409, 600/424, 429, 437–472; 128/916; 73/625, 626; 382/128; 356/614, 375.3; 324/260

(56) References Cited

U.S. PATENT DOCUMENTS

| | | | | |
|---|---|---|---|---|
| 5,447,154 A | * | 9/1995 | Cinquin et al. ............. | 600/429 |
| 5,558,091 A | * | 9/1996 | Acker et al. ................ | 600/424 |
| 5,833,608 A | * | 11/1998 | Acker ......................... | 600/409 |
| 6,019,725 A | * | 2/2000 | Vesely et al. ............... | 600/447 |
| 6,288,785 B1 | * | 9/2001 | Frantz et al. ............... | 356/614 |
| 6,306,090 B1 | | 10/2001 | Wilk | |
| 6,427,314 B1 | * | 8/2002 | Acker ......................... | 29/593 |
| 6,572,548 B2 | * | 6/2003 | Cerofolini .................. | 600/443 |

FOREIGN PATENT DOCUMENTS

| JP | 8-24263 | 1/1996 |
|---|---|---|
| WO | WO 01/06917 | 2/2001 |

* cited by examiner

Primary Examiner—Ali Imam
(74) Attorney, Agent, or Firm—Koda & Androlia

(57) ABSTRACT

An ultrasonic diagnostic apparatus 12 outputs echo data to a host controller 20. In the host controller 20, a tissue coordinate operation unit 48 computes coordinate information of a tumor 30 using a three dimensional probe 10 as an origin; a probe coordinate operation unit 52 computes coordinate information of the three dimensional probe 10 using, as its origin, an X-ray source apparatus 18 which functions as a reference position; and a combined tissue coordinate operation unit 54 uses the coordinate information of the tumor using the three dimensional probe 10 as its origin and the coordinate information of the three dimensional probe 10 using the X-ray source apparatus 18 as its origin to compute coordinate information of the tumor 30 using the X-ray source apparatus as its origin, and outputs the computed coordinate information to the X-ray source apparatus 18.

16 Claims, 8 Drawing Sheets

ULTRASONIC MEDICAL SYSTEM

BACKGROUND OF THE INVENTION

1. Field of the Invention

The present invention relates to an ultrasonic medical system, and more particularly to an ultrasonic medical system for detecting a target tissue through transmission and reception of ultrasound, and computing information regarding the position of the detected target tissue.

2. Description of Related Art

Ultrasonic diagnostic apparatuses are actively utilized in medical diagnosis and treatment. Medical methods which use an ultrasonic diagnostic apparatus so as to specify the position of a tissue to be treated include, as one example, radiation treatment involving irradiation of cancerous tumors.

In radiation treatment, intense radiation is applied to cancerous tissue to kill the tissue. Because it is desirable to minimize irradiation of normal tissue when performing such a radiation treatment, it is important that the position of a tumor tissue be precisely ascertained so as to focus the radiation accurately to the tumor tissue. In order to ascertain the tumor position, image diagnosis by means of radiography, CT (Computed Tomography), or MRI (Magnetic Resonance Imaging) is performed prior to the radiation treatment, so that the position of a tumor tissue is ascertained in advance for determining the position or range for irradiation. With such a method, however, accurate irradiation of a tumor tissue cannot be performed if the position of tumor tissue is moved due to, for example, shifting of the patient's position or the influence of breathing.

In order to overcome the above disadvantage, a radiation treatment in which the position of a tissue is ascertained using an ultrasonic diagnostic apparatus is also proposed. More specifically, in this method, radiation is directed toward a tumor tissue as the position of the tissue is being detected by an ultrasonic diagnostic apparatus. For example, Japanese Patent Laid-Open Publication No. Hei 8-24263 discloses an apparatus which uses an ultrasonic image for shock wave irradiation.

However, the above method also suffers from a problem. Specifically, since conventional ultrasonic diagnostic apparatuses obtain information regarding a tissue position using an ultrasonic probe as a reference, it may be difficult to obtain appropriate information regarding the position of the tissue, depending on the conditions in which the ultrasonic probe is used. For example, in a case wherein a doctor or other health professional holds an ultrasonic probe in their hand so as to detect a movement of a tumor tissue on a display screen of the ultrasonic diagnostic apparatus, it is not possible to determine whether detected movement is caused by a shift of the tumor tissue itself, or by a shift of the ultrasonic probe while the tumor remains still, or by combination of such movement.

Because information regarding the tissue position obtained by conventional ultrasonic diagnostic apparatuses is based on the ultrasonic probe which functions as a reference as described above, information regarding the position of a target tissue depends on the position of the ultrasonic probe.

It is therefore an advantage of the present invention to provide an ultrasonic medical system capable of outputting appropriate information regarding the tissue position.

SUMMARY OF THE INVENTION

The present invention was conceived in view of the aforementioned problems of the related art and provides an ultrasonic medical system comprising a wave transceiver for transmitting and receiving ultrasound with regard to a space including a target tissue and outputting a reception wave signal; first relative coordinate operation means for computing first relative coordinate information of the target tissue using the wave transceiver as an origin, based on the reception wave signal; second relative coordinate operation means for computing second relative coordinate information of the wave transceiver using a reference position as an origin; and combined relative coordinate operation means for computing combined relative coordinate information of the target tissue using the reference position as an origin, based on the first relative coordinate information and the second relative coordinate information, and outputting the combined relative coordinate information.

With the above configuration, because the coordinate information of the target tissue can be obtained using a desired reference position as an origin, the coordinates of the target tissue can be specified independently of the coordinates of the wave transmitter/receiver. For example, even when the wave transceiver moves or when the coordinates of the wave transceiver is not specified, the coordinates of the target tissue can be ascertained as relative coordinates with regard to the known reference position. In the above configuration, each of the first relative coordinate information and the second relative coordinate information may be synthesized information regarding a plurality of coordinate systems. For example, the second relative coordinate information may be coordinate information obtained by synthesis of the second (first) relative coordinate information and the second (second) relative coordinate information. Thus, it is possible to compute the combined relative coordinate information from three or more items of coordinate information including the third relative coordinate information, the fourth relative coordinate information, and the like, based on the same principle as used for computing the combined relative coordinate information from the first and second relative coordinate information.

Preferably, the wave transceiver transmits and receives ultrasound with regard to a three dimensional space including the target tissue, and each of the first relative coordinate information, the second relative coordinate information, and the combined relative coordinate information is three dimensional relative coordinate information. More preferably, the second relative coordinate information includes position information and direction information of the wave transceiver using the reference position as an origin.

Preferably, the above ultrasonic medical system further includes a generator which is provided at either one of a measurement origin whose positional relationship with the reference position is known and the wave transceiver, for generating a measurement signal, and a detector which is provided at the other of the measurement origin and the wave transceiver, for detecting the measurement signal, and the second relative coordinate operation means computes the second relative coordinate information of the wave transceiver using the reference position as an origin, based on the detection result by the detector. With such a configuration in which a non-contact coordinate detection configuration is achieved by the generator and the detector, the movement of the wave transceiver is not limited during coordinate detection. It should be noted that the measurement signal is a signal used for measuring the coordinates of, for example, the position of the wave transceiver. Preferably, the generator is a magnetic field generator for generating a magnetic field, and the detector is a magnetic field detector for detecting the magnetic field. With this configuration, because the magnetic field can be detected by the magnetic field detector without being blocked by a human body, it is possible to maintain the accuracy in computing the coordinates of the wave transceiver irrespective of the body position of a doctor or an examiner. Further, because magnetic fields and ultrasound do not interact with each other, influence of the magnetic field generated by the magnetic field generator on the ultrasound by the wave transceiver, or influence of the ultrasound on the magnetic fields can be disregarded.

Preferably, the first relative coordinate operation means computes the first coordinate information of the target tissue using the wave transceiver as an origin, based on coordinate information specified by an examiner by using an ultrasonic image formed based on the reception wave signal.

Preferably, the above ultrasonic medical system further comprises a holder mechanism for holding the wave transceiver and a measurement information operation unit for outputting measurement information regarding the wave transceiver which is held by the holder mechanism, and the second relative coordinate operation means computes the second relative coordinate information of the wave transceiver using the reference position as an origin, based on the measurement information. More preferably, the measurement information is coordinate information of the wave transceiver relative to a measurement origin whose positional relationship with the reference position is known. Still more preferably, the holder mechanism is an articulated robot, and the measurement information is information based on length data and angle data regarding each movable section of the articulated robot. Further preferably, the wave transceiver is brought into contact with a body surface of a patient, and the holder mechanism includes a pressure sensor for measuring a contact pressure exerted to the patient by the wave transceiver, for controlling the contact pressure to a predetermined value based on the output from the pressure sensor.

Preferably, the above ultrasonic medical system comprises a radiation source apparatus for performing irradiation with radiation while controlling an aim based on the combined relative coordinate information. With this configuration, it is possible to apply radiation intensely to the target tissue, while minimizing irradiation of tissues other than the target tissue by controlling an aim such that radiation is accurately applied to the target tissue. Therefore, the tumor can be killed while irradiation of normal tissues is reduced. As radiation, electromagnetic radiation such as X-rays and gamma-rays, and particle beams such as proton beams and deuteron beams may be used.

Preferably, the radiation source apparatus controls the aim in accordance with a movement of the target tissue based on the combined relative coordinate information. With this configuration, even when, or even as, the target tissue moves, it is possible to apply radiation intensively to the target tissue while minimizing irradiation of tissues other than the target tissue, by controlling the aim such that radiation is accurately applied to the target tissue. Therefore, the tumor can be killed while irradiation of normal tissues is reduced.

The above ultrasonic medical system may further comprise a puncture apparatus for controlling a puncture position based on the combined relative coordinate information. With such a configuration, it is possible to cause a puncture needle to reach the target tissue accurately, by introducing the puncture needle while controlling an aim such that the puncture is focused on the target tissue.

Further, in accordance with another aspect of the present invention, there is provided an ultrasonic medical system comprising an ultrasonic probe which is held by a probe holder mechanism for outputting position and direction information and is brought into contact with a body surface of a patient, the ultrasonic probe transmitting/receiving ultrasound with regard to a three dimensional space including a target tissue; an ultrasonic diagnostic apparatus for obtaining, via the ultrasonic probe, echo data for each of voxels forming the three dimensional space; and a host controller which extracts a voxel corresponding to the target tissue based on an echo level of the echo data, computes first relative coordinate information of the target tissue using the ultrasonic probe as an origin, computes second relative coordinate information of the ultrasonic probe using a reference position as an origin based on the position and direction information, and computes combined relative coordinate information of the target tissue using the reference position as an origin based on the first relative coordinate information and the second relative coordinate information and outputs the combined relative coordinate information.

Preferably, the above ultrasonic medical system further comprises a remedial beam source apparatus for performing irradiation with a remedial beam while controlling an aim in accordance with a movement of the target tissue based on the combined relative coordinate information.

BRIEF DESCRIPTION OF THE DRAWINGS

These and other advantages of the invention will be explained in the description below, in connection with the accompanying drawings, in which.

DETAILED DESCRIPTION OF THE PREFERRED EMBODIMENTS

Preferred embodiments of the present invention will be described with reference to the drawings.

[Embodiment 1]

Figure 1:
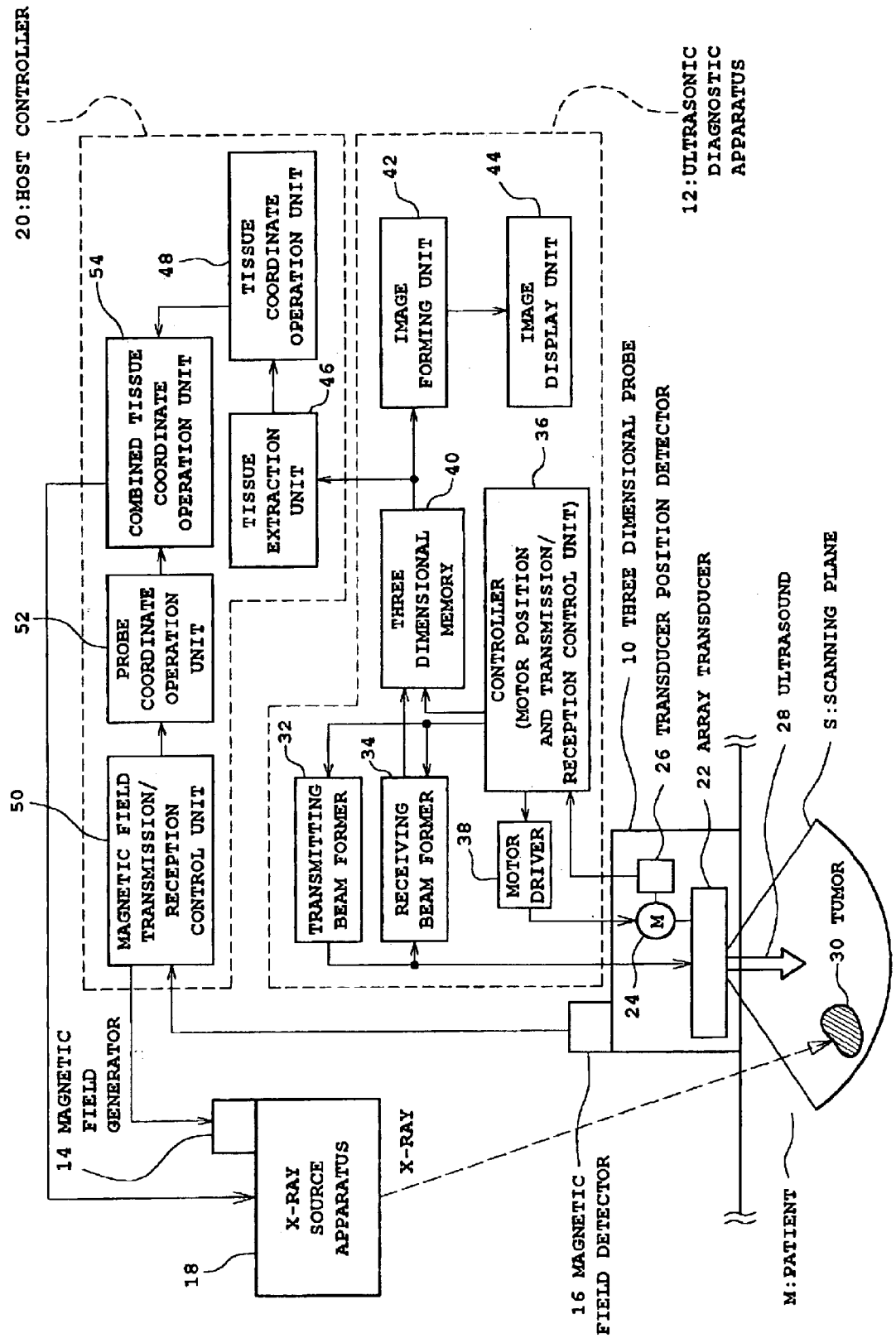
FIG. 1 is a diagram showing a configuration of an ultrasonic medical system according to the present invention.

FIG. 1 shows the overall configuration of an ultrasonic medical system according to a first embodiment of the present invention. The ultrasonic medical system shown in FIG. 1 is basically composed of a three dimensional probe (three dimensional echo data capturing probe) 10 which is a wave transceiver, an ultrasonic diagnostic apparatus 12, a magnetic field generator 14, a magnetic field detector 16, an X-ray source apparatus 18 which is a radiation source apparatus, and a host controller 20 including a first relative coordinate operator, a second relative coordinate operator, and a combined relative coordinate operator.

The three dimensional probe 10 includes an array transducer 22, a drive motor 24 for driving the array transducer 22, and a transducer position detector 26 for detecting the position of the array transducer 22. The three dimensional probe 10 is capable of transmitting and receiving ultrasound 28 with regard to a three dimensional space by causing the array transducer 22, which transmits and receives ultrasound 28, to be oscillated by the driver motor 24. The array transducer 22, which is moved to a predetermined position by the drive motor 24, effects electronic scanning to form a scanning plane S and obtains reception wave data within the scanning plane. The reception wave data thus obtained by the array transducer 22 and transducer position data detected by the transducer position detector 26 are output to the ultrasonic diagnostic apparatus 12. The array transducer 22 performs electronic scanning for transmitting and receiving ultrasound, with the scanning plane S being moved by oscillating the array transducer 22 by the drive motor 24, so that transmission/reception of ultrasound 28 is performed over the range of a scanning space.

Figure 2:
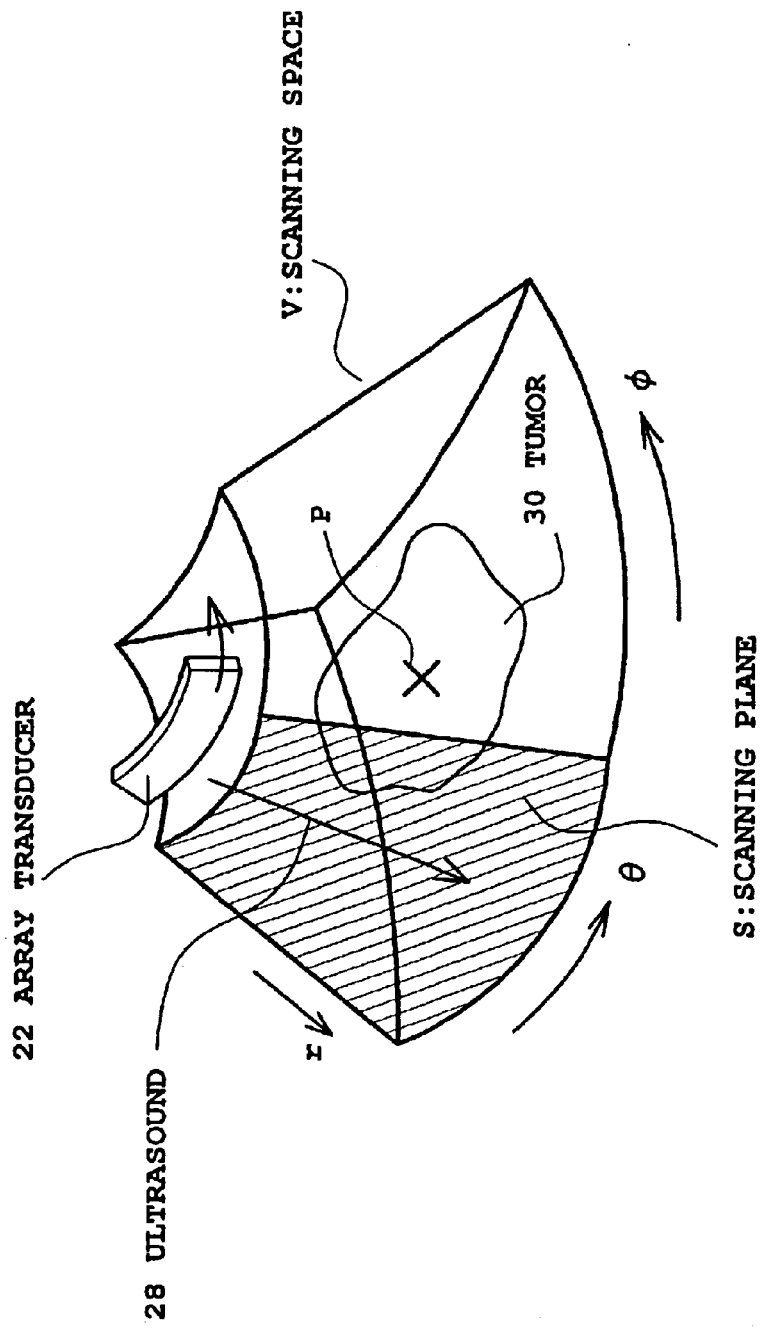
FIG. 2 is a diagram showing transmission and reception of ultrasound with regard to a three dimensional space.

FIG. 2 shows transmission/reception of the ultrasound 28 with regard to the three dimensional space. Referring to FIG. 2, the array transducer 22 transmits and receives the ultrasound 28 in the depth direction r and in the electronic scanning direction θ to form the scanning plane S. The array transducer 22 is then oscillated in the oscillation direction Φ to form a scanning space V including a tumor 30 which is a target tissue and a central point P of the tumor. It should be noted that the three dimensional echo data obtaining probe according to the present embodiment may include a two dimensional array transducer, namely a transducer which performs electronic scanning over the range of the scanning space V. Further, a probe is not limited to the three dimensional echo data obtaining probe and may also be a two dimensional echo data obtaining probe, namely a probe which transmits the ultrasound 28 only to the scanning plane S in FIG. 2.

Referring again to FIG. 1, a transmitting beam former 32 in the ultrasonic diagnostic apparatus 12 controls a transmission drive signal to be supplied to the array transducer 22 for forming the ultrasound 28 via the three dimensional probe 10. A receiving beam former 34 collects reception wave data supplied from the array transducer 22 for forming echo data. A controller (motor position and transmission/reception control unit) 36 drives the drive motor 24 for the array transducer 22 and also obtains oscillation position data of the array transducer 22 from the transducer position detector 26, thereby controlling the oscillation position of the array transducer 22. The controller 36 further controls the transmitting beam former 32 and the receiving beam former 34 to form the ultrasound 28 and collect the reception wave data of the array transducer 22 at each oscillation position. More specifically, the controller 36, by controlling the transmitting beam former 32, the receiving beam former 34, and the array transducer drive motor 24, transmits the ultrasound 28 to a desired three dimensional space and obtains echo data for each of voxels forming the three dimensional space. The echo data for each voxel is designated with an address corresponding to relative coordinates using the three dimensional probe 10 as a reference. The echo data is then written into a three dimensional memory 40 and is also output to the host controller 20. The echo data is simultaneously output to an image forming unit 42 within the ultrasonic diagnostic apparatus 12 for forming an ultrasonic image, which is then displayed in an image display unit 44 in the form of a three dimensional ultrasonic image or the like.

The host controller 20 includes a tissue extraction unit 46 and a tissue coordinate operation unit 48 which constitute the first relative coordinate operator, a magnetic field transmission/reception control unit 50 and a probe coordinate operation unit 52 which constitute the second relative coordinate operator, and a combined tissue coordinate operation unit 54 which is a combined relative coordinate operator. A part or all of these elements forming the host controller 20 may be incorporated in the ultrasonic diagnostic apparatus 12 or the X-ray source apparatus 18.

The tissue extraction unit 46 extracts the tumor 30 which is a target tissue, based on the echo data within the three dimensional space which is written in the three dimensional memory 40. In one example extraction method, echo levels are previously obtained as echo data, and the echo levels are used to discriminate the tumor 30 from normal tissue. More specifically, the echo level for each echo data written in the three dimensional memory 40 is compared with a predetermined level which corresponds to a border between the echo levels of the tumor 30 and the echo levels of normal tissues to determine echo data portions corresponding to the echo levels of the tumor 30 as the tumor 30. Because each echo data is designated with an address corresponding to relative coordinates using the three dimensional probe 10 as a reference before the data is written in the three dimensional memory 40 as described above, it is possible to determine the relative coordinates of the echo data which corresponds to the tumor 30. However, methods other than the above method may be adopted for discriminating the tumor. For example, image analysis such as a texture analysis may be used.

The tissue coordinate operation unit 48 computes target tissue coordinates using the three dimensional probe 10 as a reference, based on the relative coordinates of the extracted echo data portion corresponding to the tumor 30 using the three dimensional probe 10 as a reference. The target tissue coordinates may be obtained for just the central point of the tumor 30 by computing the position of a gravity center of the tumor 30 from the outer surface coordinates of the extracted tumor 30 portion. Alternatively, all of the relative coordinates which have been determined as the tumor 30 may be output as the target tissue coordinates. Further, a position on the ultrasonic image of the target tissue displayed on the image display unit 44, which is designated by the examiner who is observing the ultrasonic image may be determined as the target tissue coordinates. In any case, the coordinates of the extracted target tissue use the three dimensional probe 10 as a reference, because the ultrasound 28 is transmitted and received using the three dimensional probe 10 as a reference. In the following description, a case wherein the coordinates for only the central point of the tumor 30 is output as the target tissue coordinates will be explained.

The magnetic field transmission/reception control unit 50 controls the magnetic field generator 14 mounted on the X-ray source apparatus 18 to generate magnetic field distribution in a room for measuring information regarding the position of the three dimensional probe 10. The magnetic field transmission/reception control unit 50 also controls the magnetic field detector 16 mounted on the three dimensional probe 10 to detect the magnetic field distribution generated within the room. More specifically, the magnetic field generator 14 has three magnetic field generating coils whose axial directions correspond respectively to three directions which are orthogonal to each other, for generating magnetic field distribution. The magnetic field detector 16 also includes three magnetic field detecting coils whose axial directions correspond respectively to three directions which are orthogonal to each other. The magnetic field generator 14 and the magnetic field detector 16 are configured to allow detection of not only information regarding the position of the magnetic field detector 16 relative to the magnetic field generator 14 but also information regarding the direction of the magnetic field detector 16. The information regarding the position of the three dimensional probe 10 (coordinate information) is thus measured by means of the magnetic field generator 14 and the magnetic field detector 16. Information regarding the position and the direction can be detected using any appropriate known method.

The method of detecting the coordinate information of the three dimensional probe 10 is not limited to the detection method using the magnetic field generator 14 and the magnetic field detector 16 as described above, and any other appropriate methods may be used. For example, not just a magnetic field, but light, acoustic waves, or radio waves may be used for detection. When detection by means of light is performed, a light signal generator and a light detector are used in place of the magnetic field generator 14 and the magnetic field detector 16, respectively. The light signal generator generates light with a distribution such that the intensity of the generated light is different at different positions in the room, which is then detected by the light detector. At this time, the light detector is fixed on the three dimensional probe 10 at three different points, and, by detecting the positions of the three points, it is possible to use triangulation to compute not only position information but also direction information regarding the three dimensional probe 10. Further, it is obvious that when the generator is mounted on the three dimensional probe 10 and the detector is mounted at a reference position, it is also possible to compute the position information and the direction information of the three dimensional probe 10 with respect to the reference position according to the same principle.

The probe coordinate operation unit 52 computes the position and direction information of the magnetic field detector 16 using the magnetic field generator 14 as a reference, based on the detection result output from the magnetic field transmission/reception control unit 50. The detection result output from the magnetic field transmission/reception control unit 50 is based on position information and direction information of the magnetic field detector 16 relative to the magnetic field generator 14. Therefore, by mounting the magnetic field generator 14 at a desired position, such as at the origin of the X-ray source apparatus 18 for example, and mounting the magnetic field detector 16 at the origin of the three dimensional probe 10, it is possible to directly detect information regarding the position and direction of the three dimensional probe 10 relative to the origin of the X-ray source apparatus 18. Due to the design limitation, however, there are cases wherein the magnetic field generator 14 cannot be mounted at the origin position of the X-ray source apparatus 18 or wherein the magnetic field detector 16 cannot be mounted at the origin position of the three dimensional probe 10. These cases will be described with reference to FIG. 3.

Figure 3:
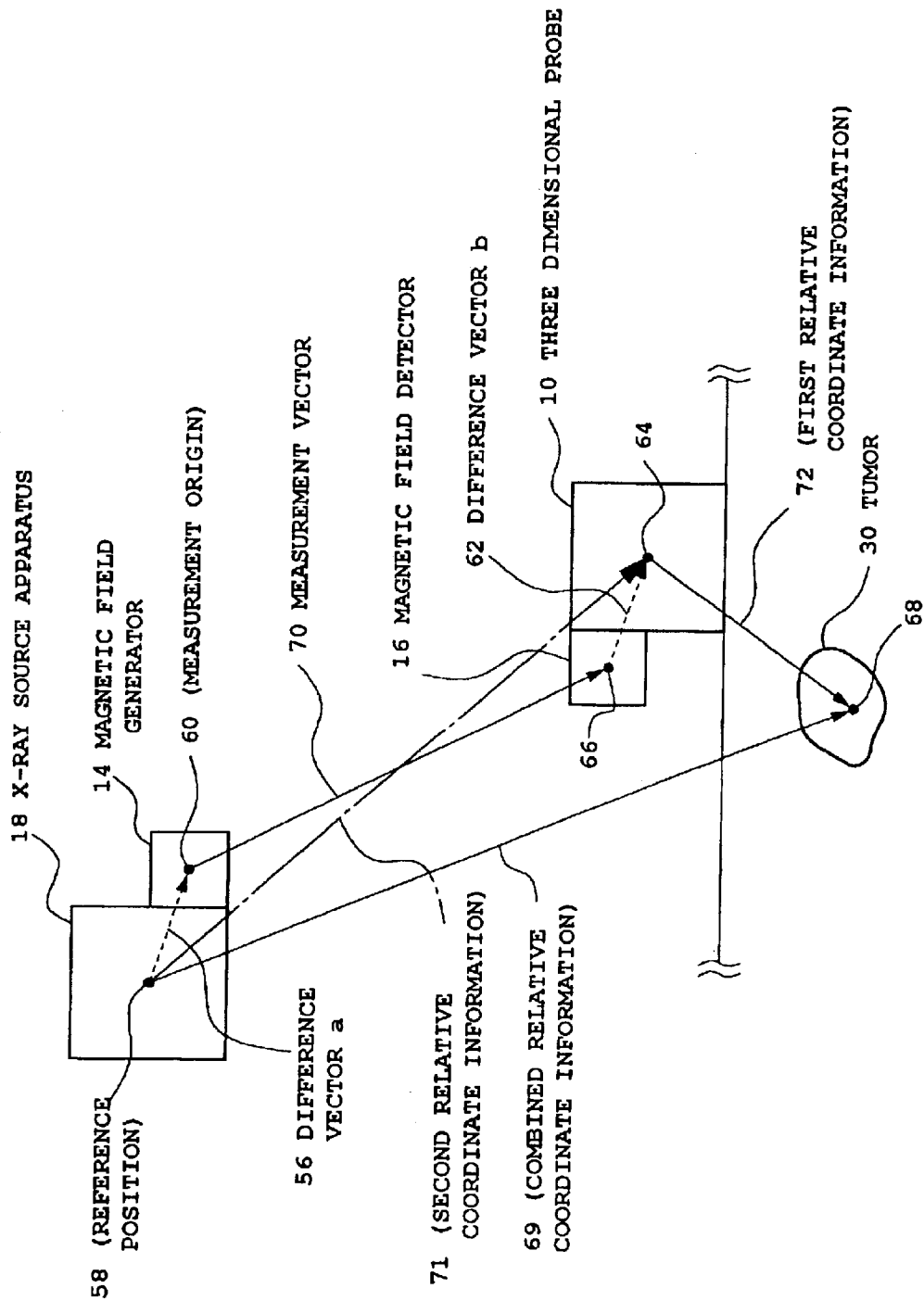
FIG. 3 is a diagram showing a relationship between position vectors in the present invention.

Referring to FIG. 3, a difference vector a 56 indicates a deviation between the origin position 58 of the X-ray source apparatus 18 which functions as a reference position for X-ray irradiation and a magnetic field generator position 60 which corresponds to a measurement origin for measuring the position and direction of the three dimensional probe 10. Further, a difference vector b 62 indicates a deviation between the origin position 64 of the three dimensional probe 10 and a magnetic field detector position 66. The detection result output from the magnetic field transmission/reception control unit 50 (see FIG. 1) is a measurement vector 70 corresponding to a relative position vector of the magnetic field detector position 66 relative to the magnetic field generator position 60. Further, the coordinate information output from the tissue coordinate operation section 48 (see FIG. 1) is an ultrasound detection vector (the first relative coordinate information) 72 corresponding to a relative position vector of the tumor position 68 relative to the origin position 64 of the three dimensional probe 10.

Accordingly, in order to obtain a combined vector (combined relative coordinate information) 69 indicating the tumor position 68 using the origin position 58 of the X-ray source apparatus as a reference, it is necessary to compute a probe position vector (the second relative coordinate information) 71 by adding the difference vector a 56 and the difference vector b 62 to the measurement vector 70 and then add the ultrasound detection vector 72 to the computed probe position vector 71. Because the magnetic field generator 14 and the magnetic field detector 16 are fixed to the X-ray source apparatus 18 and to the three dimensional probe 10, respectively, both the difference vector a 56 and the difference vector b 62 are fixed vectors and can therefore be measured prior to the measurement of the position 68 of the tumor which is a target tissue.

When computing the coordinates of the tumor position 68, by performing coordinate transformation based on these difference vectors a 56 and b 62 which have been measured in advance, it is possible to process the origin position 58 of the X-ray source apparatus 18 and the magnetic field generator position 60 equivalently and also process the origin position 64 of the three dimensional probe 10 and the magnetic field detector position 66 equivalently. In the following description, it is assumed that such coordinate transformation has been performed so that the coordinate system having an origin corresponding to the origin position 58 of the X-ray source apparatus 18 matches the coordinate system having an origin corresponding to the magnetic field generator position 60, and such that the coordinate system having an origin corresponding to the origin position 64 of the three dimensional probe 10 matches the coordinate system having an origin corresponding to the magnetic field detector position 66.

Referring back to FIG. 1, the combined tissue coordinate operation unit 54 computes coordinates of the target tissue relative to the origin of the X-ray source apparatus 18 based on the coordinate information of the target tissue with the three dimensional probe 10 being used as its origin, which is output from the tissue coordinate operation unit 48 and the position and direction information of the three dimensional probe 10 relative to the origin of the X-ray source apparatus 18 which is output form the probe coordinate operation unit 52. At this point, it is assumed that coordinate transformation between the magnetic field generator 14 and the X-ray source apparatus 18 and between the magnetic field detector 16 and the three dimensional probe 10 has been performed in the probe coordinate operation unit 52, as described above. In other words, the coordinates having an origin corresponding to the magnetic field generator position and the coordinates having an origin corresponding to the X-ray source apparatus position coincide with each other, and the coordinates having an origin corresponding to the magnetic field detector position and the coordinates having an origin corresponding to the three dimensional probe position coincide with each other.

Figure 4:
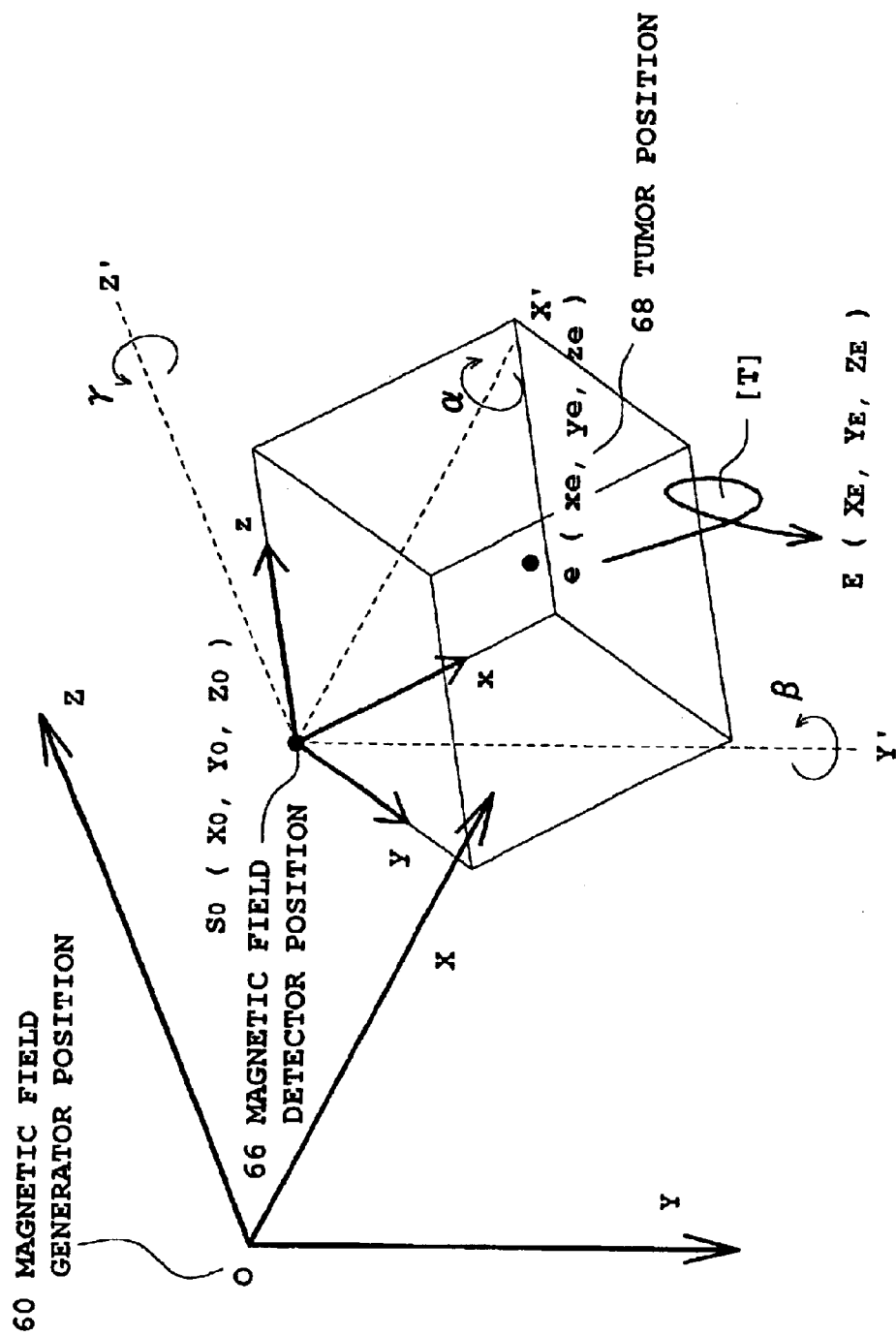
FIG. 4 is a diagram showing a relationship between coordinate systems in the present invention.

A computation method in the combined tissue coordinate operation unit 54 will be described with reference to FIG. 4. Referring to FIG. 4, a coordinate system (X, Y, Z) is a coordinate system which is fixed to the magnetic field generator 14 having an origin at the magnetic field generator position 60, and corresponds to the coordinate system using the X-ray source apparatus 18 as a reference. A coordinate system (x, y, z) is a coordinate system which is fixed to the magnetic field detector 16 having an origin at the magnetic field detector position 66, and corresponds to the coordinate system using the three dimensional probe 10 as a reference. Here, the origin of the coordinate system (x, y, z) corresponding to the magnetic field detector position 66 when the coordinate system (X, Y, Z) is used as a reference, is represented by So(Xo, Yo, Zo). A point e indicates the position of a tumor which is a target tissue and is represented by e(xe, ye, ze) relative to the coordinate system (x, y, z) which is a reference. Further, axes X', Y', and Z' which are parallel to the X axis, the Y axis and the Z axis respectively, are provided, for which a coordinate system having the point So as its origin is represented by coordinate system (X', Y', Z').

The positional relationship between the coordinate system (x, y, z) and the coordinate system (X', Y', Z') is such that when the coordinate system (X', Y', Z') is rotated in the order of X' axis, Y' axis, and then Z' axis by α degree, β degree, and γ degree, respectively, the X' axis coincides with the x axis, the Y' axis coincides with the y axis, and the Z' axis coincides with the z axis. As described above, the information regarding the position and direction of the magnetic field detector using the magnetic field generator as a reference has been computed in the probe coordinate operation unit 52. More specifically, the origin position information (Xo, Yo, Zo) of the coordinate system (x, y, z) relative to the coordinate system (X, Y, Z) and the six dimensional information of the direction information (α, β, γ) have been computed in the probe coordinate operation unit 52. The coordinate transformation from the coordinate system (x, y, z) to the coordinate system (X', Y', Z') can then be expressed by the following expression.

[Expression 1]

$$[X'\ Y'\ Z'\ 1] = [x\ y\ z\ 1] \begin{bmatrix} 1 & 0 & 0 & 0 \\ 0 & \cos\alpha & \sin\alpha & 0 \\ 0 & -\sin\alpha & \cos\alpha & 0 \\ 0 & 0 & 0 & 1 \end{bmatrix}$$

$$\begin{bmatrix} \cos\beta & 0 & -\sin\beta & 0 \\ 0 & 1 & 0 & 0 \\ \sin\beta & 0 & \cos\beta & 0 \\ 0 & 0 & 0 & 1 \end{bmatrix} \begin{bmatrix} \cos\gamma & \sin\gamma & 0 & 0 \\ -\sin\gamma & \cos\gamma & 0 & 0 \\ 0 & 0 & 1 & 0 \\ 0 & 0 & 0 & 1 \end{bmatrix}$$

Further, coordinate transformation from the coordinate system (X', Y', Z') to the coordinate system (X, Y, Z) can be expressed as follows:

[Expression 2]

$$[X\ Y\ Z\ 1] = [X'\ Y'\ Z'\ 1] \begin{bmatrix} 1 & 0 & 0 & 0 \\ 0 & 1 & 0 & 0 \\ 0 & 0 & 1 & 0 \\ X_0 & Y_0 & Z_0 & 1 \end{bmatrix}$$

According to the above expressions 1 and 2, coordinate transformation from the coordinate system (x, y, z) to the coordinate system (X, Y, Z) can be expressed as follows:

[Expression 3]

$$[X\ Y\ Z\ 1] = [x\ y\ z\ 1][T]$$

$$[T] = \begin{bmatrix} 1 & 0 & 0 & 0 \\ 0 & \cos\alpha & \sin\alpha & 0 \\ 0 & -\sin\alpha & \cos\alpha & 0 \\ 0 & 0 & 0 & 1 \end{bmatrix} \begin{bmatrix} \cos\beta & 0 & -\sin\beta & 0 \\ 0 & 1 & 0 & 0 \\ \sin\beta & 0 & \cos\beta & 0 \\ 0 & 0 & 0 & 1 \end{bmatrix}$$

$$\begin{bmatrix} \cos\gamma & \sin\gamma & 0 & 0 \\ -\sin\gamma & \cos\gamma & 0 & 0 \\ 0 & 0 & 1 & 0 \\ 0 & 0 & 0 & 1 \end{bmatrix} \begin{bmatrix} 1 & 0 & 0 & 0 \\ 0 & 1 & 0 & 0 \\ 0 & 0 & 1 & 0 \\ X_0 & Y_0 & Z_0 & 1 \end{bmatrix}$$

Accordingly, using the above coordinate transformation matrix [T], the coordinate transformation can be performed from the coordinate system (x, y, z) to the coordinate system (X, Y, Z), in other words from the coordinate system using the magnetic field detector as a reference to the coordinate system using the magnetic field generator as a reference.

Referring again to FIG. 1, the combined tissue coordinate operation unit 54 sets up the transformation matrix [T] based on the information regarding the position and direction of the magnetic field detector 16 (three dimensional probe 10) using the magnetic field generator 14 (X-ray source apparatus 18) as a reference, which is output from the probe coordinate operation unit 52. Then, the transformation matrix is used to transform the coordinate information output from the tissue coordinate operation unit 48 regarding the position 68 of the tumor which is a target tissue with the magnetic field detector 16 (three dimensional probe 10) being used as its origin into the coordinate information in the coordinate system using the magnetic field generator 14, namely the X-ray source apparatus 18, as a reference. The position information for the target tissue using the X-ray source apparatus as a reference 18 which has been thus computed is output from the host controller 20 to the X-ray source apparatus 18.

Figure 5:
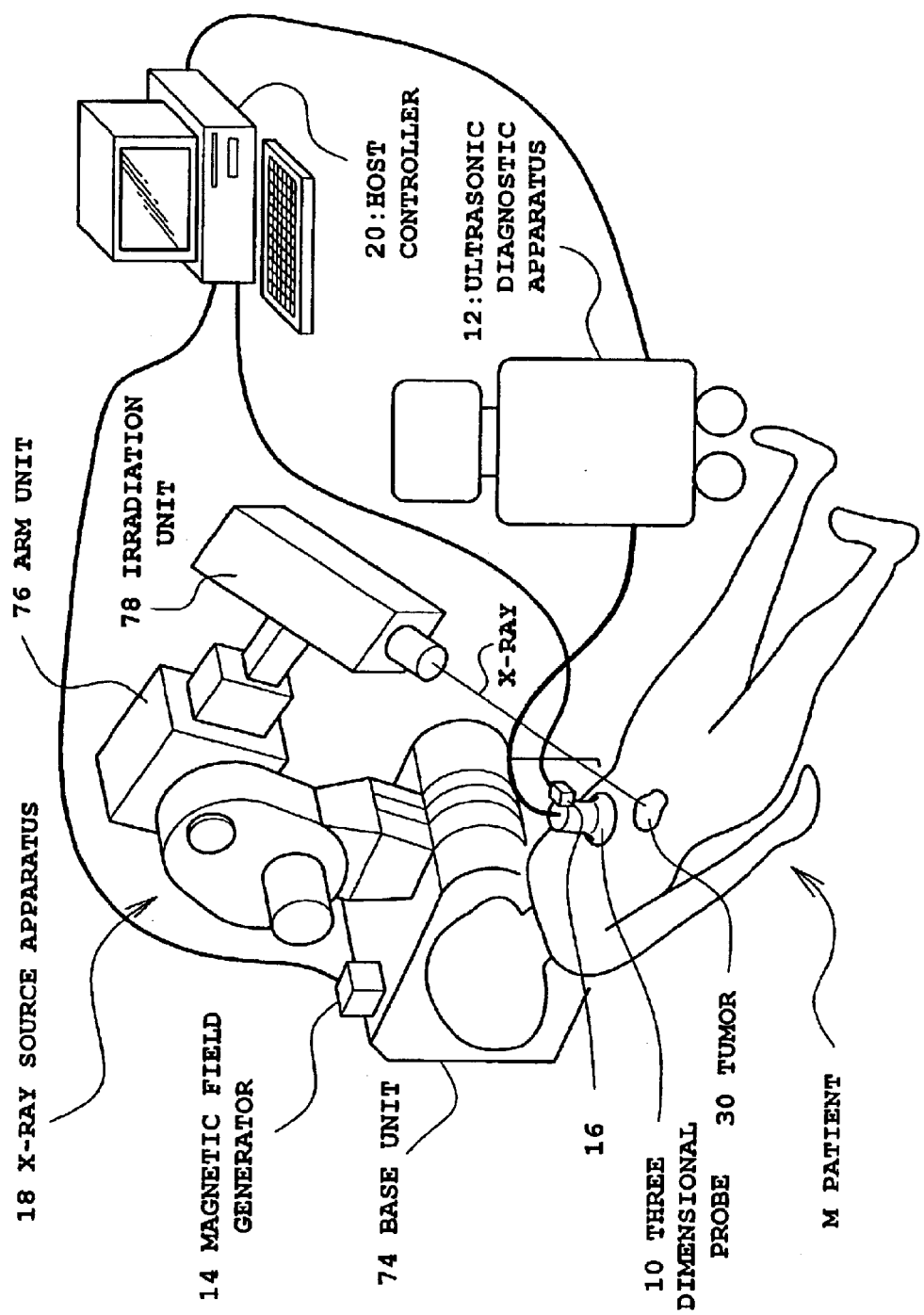
FIG. 5 is a diagram showing a remedial method utilizing an ultrasonic medical system according to the present invention.

FIG. 5 shows a remedial method using the ultrasonic medical system shown in FIG. 1. The ultrasonic diagnostic apparatus 12, the three dimensional probe 10, the magnetic field generator 14, the magnetic field detector 16, and the host controller 20 operate as described above, so that the information regarding the position of the tumor 30 with the X-ray source apparatus 18 being used as a reference is output from the host controller 20 to the X-ray source apparatus 18. The X-ray source apparatus 18 controls an arm unit 76 and an irradiation unit 78 based on the position information of the tumor 30 such that X-ray is intensively applied onto the tumor 30 located within the body of a patient M. Further, by controlling the aim in accordance with the movement of the tumor 30, it is possible to apply intense X-ray radiation to just the tumor, while minimizing irradiation of normal tissues, even as the position of tumor moves. When the aim is controlled in accordance with the movement of the tumor 30, it is desirable to continuously detect the tumor 30 by the three dimensional probe 10 during the X-ray irradiation. In this case, the three dimensional probe 10 may be held by a doctor or other person, or may be fixed to a fixing apparatus which is separately provided for the three dimensional probe 10. When a doctor or other user holds the three dimensional probe 10 for performing X-ray irradiation, certain measures must be taken, such as that the examiner puts on an X-ray protector, for example. Further, although the magnetic field generator 14 is mounted on a base unit 74 of the X-ray source apparatus in FIG. 5, the location where the magnetic field generator 14 is provided may be appropriately selected according to the usage situation, and the magnetic field generator 14 may be fixed at another position in the room.

[Embodiment 2]

Figure 6:
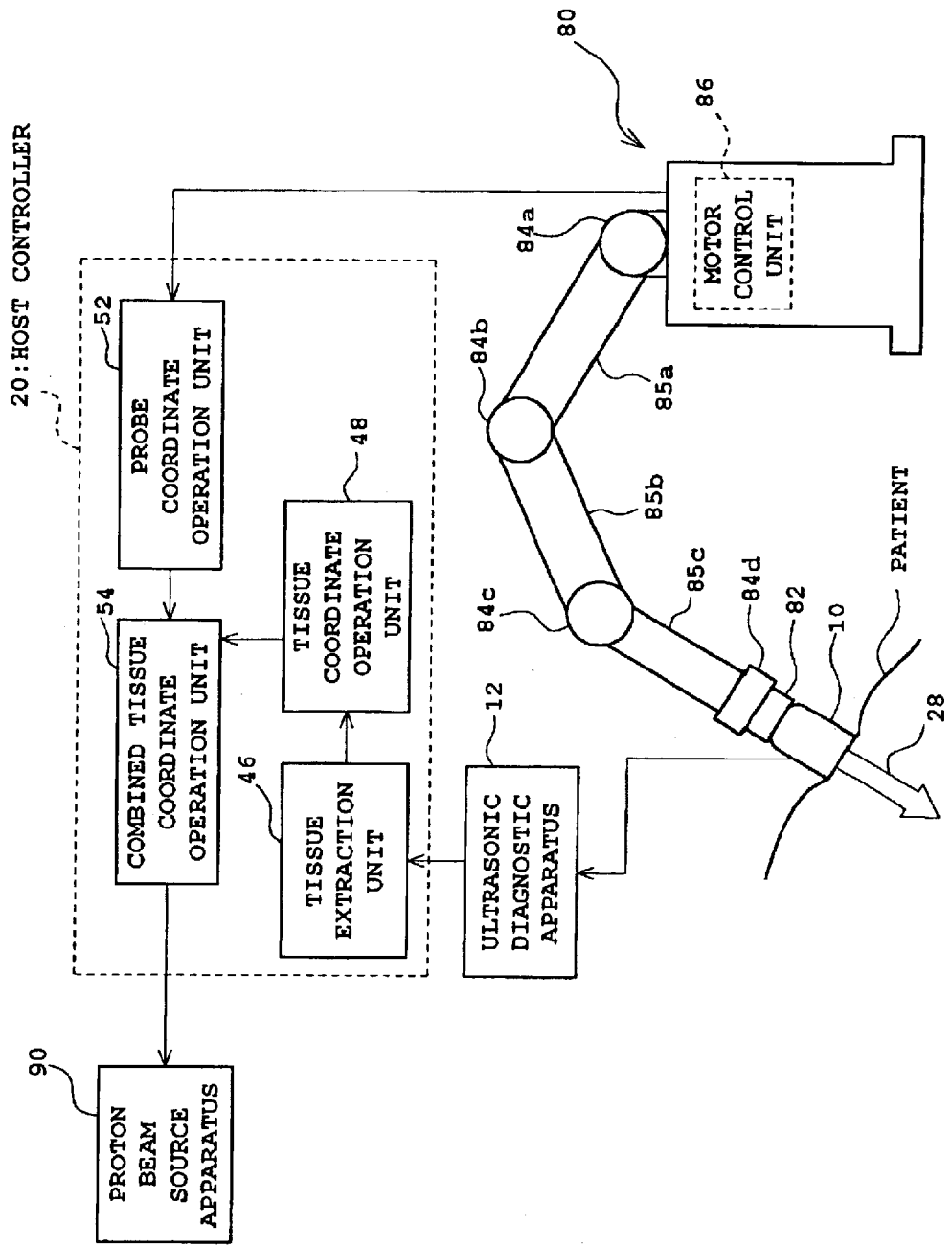
FIG. 6 is a diagram showing a configuration of an ultrasonic medical system according to another embodiment of the present invention.

FIG. 6 shows the overall configuration of an ultrasonic medical system according to a second embodiment of the present invention. In rough terms, the ultrasonic medical system shown in FIG. 6 includes a three dimensional probe (three dimensional echo data capturing probe) 10 which is a wave transceiver, an articulated robot 80, an ultrasonic diagnostic apparatus 12, a proton beam source apparatus 90, and a host controller 20 having a first relative coordinate operator, a second relative coordinate operator, and a combined relative coordinate operator.

The three dimensional probe 10 and the ultrasonic diagnostic apparatus 12 are the same as those shown in FIG. 1 regarding the first embodiment. More specifically, the ultrasonic diagnostic apparatus 12 transmits ultrasound 28 into a three dimensional space within a patient's body via the three dimensional probe 10, collects reception wave data for obtaining echo data, and displays a three dimensional ultrasonic image formed based on the obtained echo data on the image display. The obtained echo data is also output to the host controller 20.

The articulated robot 80 holding the three dimensional probe 10 moves to a diagnostic position on a surface of the patient's body, and also changes the direction of the three dimensional probe 10. The three dimensional probe 10 is attached to a probe attachment 82 and changes its position and direction when drive units 84a to 84d are driven. A drive motor (not shown) is provided in each of the drive units 84a to 84d for driving arms 85a to 85c. The operation of each drive motor is controlled by a motor control unit 86. The three dimensional probe 10 held by the articulated robot 80 transmits and receives ultrasound 28 with regard to the three dimensional space within the patient's body containing the tumor.

The motor control unit 86 controls each drive motor within each of the drive units 84a to 84d based on a user operation. The motor control unit 86 may control each drive motor such that the arms automatically follow the movement of the tumor. Further, a pressure sensor (not shown) is provided in the probe attachment 82 for detecting the pressure exerted on the surface of the patient's body when the three dimensional probe 10 is brought into contact with the body surface and outputting the detected pressure to the motor control unit 86. Then, the motor control unit 86 controls each drive motor so as to maintain the pressure exerted onto the surface of the patient's body to a fixed value, for example, thereby preventing an excessive pressure applied to the patient. The articulated robot 80 outputs the motor driving information indicating the drive states of the drive units 84a to 84d to the host controller 20.

The motor driving information output from the articulated robot 80 will be described. Assuming that the disposition location of the articulated robot 80 (the central point on the bottom portion of the articulated robot 80, for example) is a measurement origin, the drive unit 84a is located at a fixed position relative to the measurement origin. The drive unit 84a is connected to one end of the arm 85a for turning or moving upward and downward the arm 85a to thereby set an angle of the arm 85a. The other end of the arm 85a is connected to the drive unit 84b. Therefore, the position of the drive unit 84b relative to the measurement origin is determined by the length and angle of the arm 85a. Accordingly, based on the motor driving information (the angle data of the arm 85a) corresponding to the drive unit 84a, the articulated robot 80 outputs a transformation matrix Ta for deriving the position coordinates (Xb, Yb, Zb) of the drive unit 84b relative to the measurement origin from the measurement origin coordinates (Xr, Yr, Zr).

The drive unit 84b is connected to one end of the arm 85b for moving the arm 85b upward and downward. The other end of the arm 85b is connected to the drive unit 84c. Therefore, the position of the drive unit 84c relative to the drive unit 84b is determined by the length and angle of the arm 85b. Accordingly, based on the motor driving information (the angle data of the arm 85b) corresponding to the drive unit 84b, the articulated robot 80 outputs a transformation matrix Tb for deriving the position coordinates (Xc, Yc, Zc) of the drive unit 84c relative to the measurement origin from the position coordinates (Xb, Yb, Zb) of the drive unit 84b.

The position of the drive unit 84d relative to the drive unit 84c is determined by the length and angle of the arm 85c. Accordingly, based on the motor driving information (the angle data of the arm 85c) corresponding to the drive unit 84c, the articulated robot 80 outputs a transformation matrix Tc for deriving the position coordinates (Xd, Yd, Zd) of the drive unit 84d relative to the measurement origin from the position coordinates (Xc, Yc, Zc) of the drive unit 84c. Further, because the three dimensional probe 10 turns in accordance with the turning of the drive unit 84d, the articulated robot 80 outputs, based on the motor driving information corresponding to the drive unit 84d, a transformation matrix Td for deriving the coordinates of the origin position (Xs, Ys, Zs) of the three dimensional probe 10 relative to the measurement origin from the position coordinates (Xd, Yd, Zd) of the drive unit 84d. Thus, the transformation matrices Ta, Tb, Tc, and Td representing the holding state of the three dimensional probe 10 is output to the probe coordinate operation unit 52 of the host controller 20.

The probe coordinate operation unit 52 then computes the position and direction of the three dimensional probe 10 relative to the measurement origin (the disposition location of the articulated robot 80), based on the motor driving information output from the articulated robot 80. The position coordinates (Xs, Ys, Zs) of the three dimensional probe 10 relative to the measurement origin is computed by the following expression.

$$[Xs, Ys, Zs, 1] = [Xr, Yr, Zr, 1][Ta][Tb][Tc][Td] \quad \text{[Expression 4]}$$

wherein Ta, Tb, Tc, and Td are transformation matrices based on the motor driving information output from the articulated robot 80, and (Xr, Yr, Zr) indicates coordinates of the measurement origin.

Here, the direction of the three dimensional probe 10 can be computed from the position coordinates (Xd, Yd, Zd) of the drive unit 84d and the position coordinates (Xs, Ys, Zs) of the three dimensional probe 10. More specifically, it is possible to obtain the line connecting these coordinates (Xs, Ys, Zs) and (Xd, Yd, Zd) and obtain the direction of the three dimensional probe 10 along that line. In this manner, the probe coordinate operation unit 52 computes the position and direction of the three dimensional probe 10 relative to the measurement origin.

The tissue extraction unit 46 and the tissue coordinate operation unit 48 in the host controller 20 operate similarly to those in the first embodiment (see FIG. 1). More specifically, the tissue extraction unit 46 extracts a tumor based on echo data within the three dimensional space which is output from the ultrasonic diagnostic apparatus 12 for determining relative coordinates of echo data corresponding to the tumor. The tissue coordinate operation unit 48 then computes coordinates of the central point of the tumor using the three dimensional probe 10 as a reference.

The combined tissue coordinate operation unit 54 uses the coordinate information of the central point of the tumor having an origin at the three dimensional probe 10, which is output from the tissue coordinate operation unit 48, and the information regarding the position and direction of the three dimensional probe 10 relative to the measurement point which is output from the probe coordinate operation unit 52, to compute the coordinates of the central point of the tumor relative to the origin of the proton beam source apparatus 90. The computation performed by the combined tissue coordinate operation unit 54 will be described.

Figure 7:
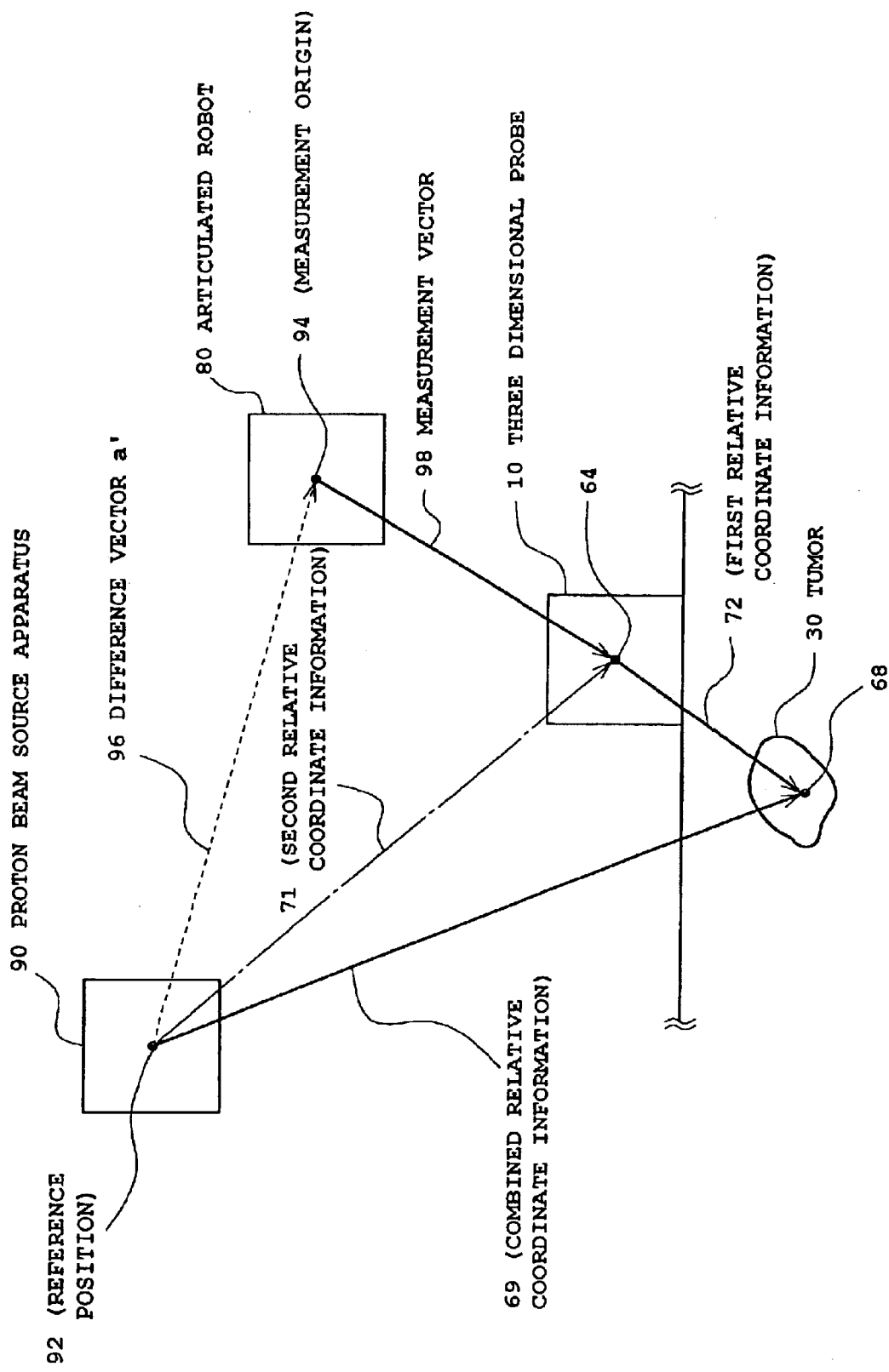
FIG. 7 is a diagram showing a relationship between positional vectors in the present invention.

FIG. 7 is a diagram for explaining the computation performed by the combined tissue coordinate operation unit 54. It is assumed that the reference position for proton beam irradiation is an origin position 92 of the proton beam source apparatus 90 and that the measurement origin for measuring the position and direction of the three dimensional probe is a bottom central point 94 of the articulated robot 80. Further, a position vector of the bottom central point (measurement origin) 94 relative to the origin position (reference position) 92 is assumed to be a difference vector a' 96. The coordinate information output from the probe coordinate operation unit 52 (see FIG. 6) is a measurement vector 98 which corresponds to a relative position vector of the origin position 64 relative to the bottom central point 94, and the coordinate information output from the tissue coordinate operation unit 48 is an ultrasound detection vector (the first relative coordinate information) 72 which corresponds to a relative position vector of the tumor position 68 relative to the origin position 64 of the three dimensional probe 10.

Accordingly, in order to compute a combined vector (combined relative coordinate information) indicating the coordinates of the tumor position 68 using the origin position 92 of the proton beam source apparatus 90 as a reference, it is necessary to first compute a probe position vector (second relative coordinate information) 71 by adding the measurement vector 98 and the difference vector a' 96, and to then add the computed probe position vector 71 with the ultrasound detection vector 72. The difference vector a' 96 is a known vector because the state in which the articulated robot 80 and the proton beam source apparatus 90 are arranged is known. It is therefore possible to measure the difference vector a' 96 in advance, prior to the measurement of the position 68 of the tumor which is the target tissue.

Referring back to FIG. 6, the information regarding the coordinates of the tumor relative to the reference position, such as the coordinates of the central point of the tumor, which is computed by the combined tissue coordinate operation unit 54 is output to the proton beam source apparatus 90, which then directs proton beams toward the position corresponding to the coordinates of the central point of the tumor.

Figure 8:
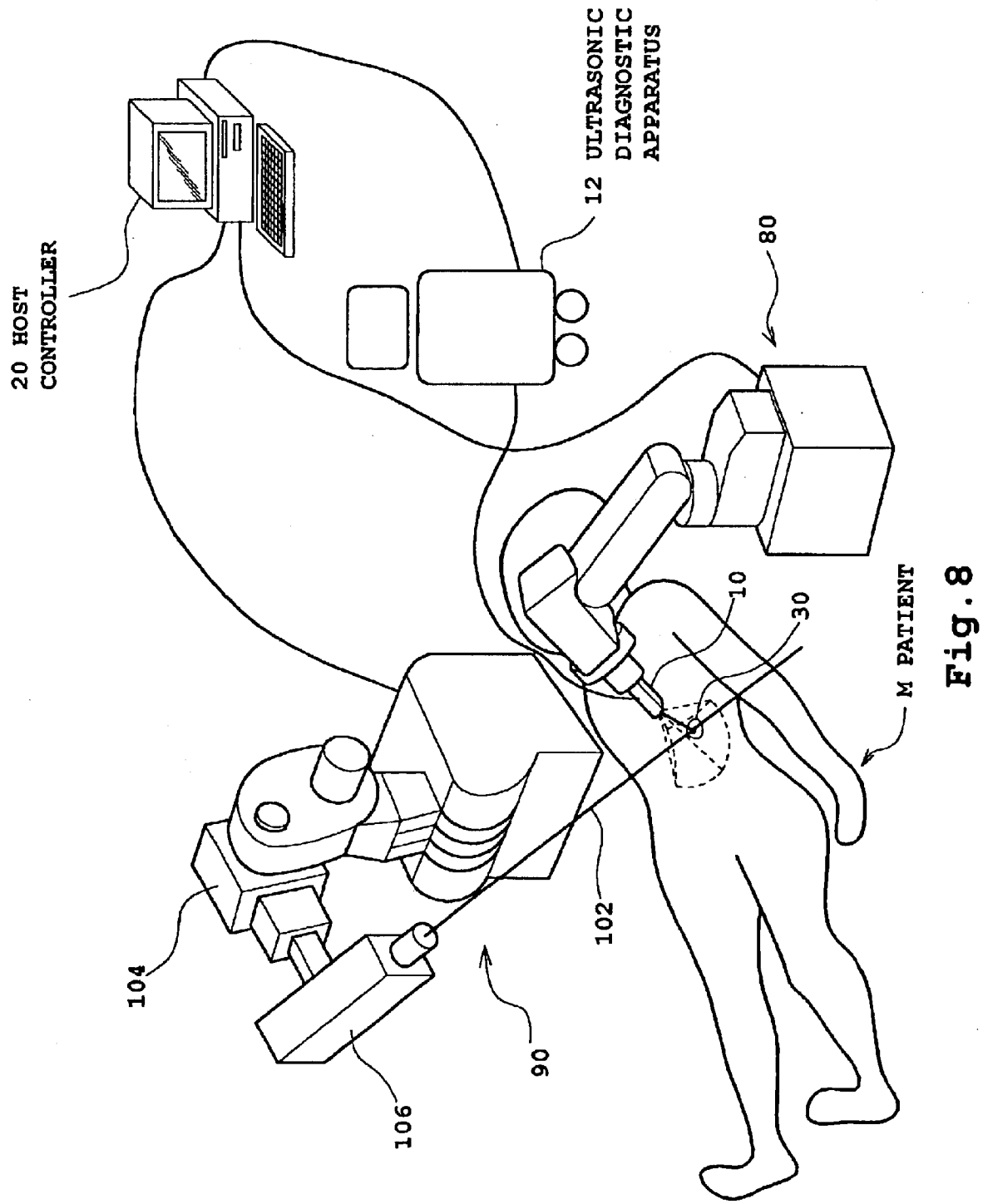
FIG. 8 is a diagram showing a remedial method utilizing an ultrasonic medical system according to the present invention.

FIG. 8 shows a remedial method using the ultrasonic medical system shown in FIG. 6. The ultrasonic diagnostic apparatus 12, the articulate robot 80, and the host controller 20 operate as described with reference to FIG. 6, so that the information regarding the position of the tumor 30 relative to the reference position is output from the host controller 20 to the proton beam source apparatus 90. Based on the position information of the tumor 30, the proton beam source apparatus 90 controls an arm unit 104 and an irradiation unit 106 for applying proton beams 10 intensively to a tumor 30 within a patient M. Further, the proton beam source apparatus 90 controls the aim in accordance with the movement of the tumor 30, so that proton beams can be intensively delivered to just the tumor 30, while irradiation of normal tissues is minimized, even when the tumor moves. It should be noted that while the reference position is set to the origin position of the proton beam source apparatus 90 in the example shown in FIGS. 6 and 8, the reference position may be appropriately selected in accordance with actual usage, such as at a predetermined location in a room in which the treatment is being carried out.

In addition, other radiation source apparatuses including a lithotomic apparatus may be used in place of the X-ray source apparatus 18 and the proton beam source apparatus 90 for the remedial method using the ultrasonic medical system according to the present invention. It is, of course, possible to use remedial beams other than radiation. A medical method utilizing a puncture apparatus which inserts a puncture needle toward the target tissue may also be used. In any case, control of various remedial beam irradiation or puncture needle insertion is performed based on the information regarding the position of the target tissue using a desired reference position as an origin.

As described above, according to the ultrasonic medical system according to the present invention, appropriate information regarding the tissue position can be obtained.

While the preferred embodiments of the present invention have been described using specific terms, such description is for illustrative purposes only, and it is to be understood that changes and variations may be made without departing from the spirit or scope of the appended claims.

What is claimed is:

1. An ultrasonic medical system comprising:
    a wave transceiver for transmitting and receiving ultrasound with regard to a space including a target tissue and for outputting a reception wave signal;
    first relative coordinate operation means for computing first relative coordinate information of the target tissue using the wave transceiver as an origin, based on an output reception wave signal;
    second relative coordinate operation means for computing second relative coordinate information of the wave transceiver using a reference position as an origin; and
    combined relative coordinate operation means for computing combined relative coordinate information of the target tissue using the reference position as an origin, based on the first relative coordinate information and the second relative coordinate information, and outputting the combined relative coordinate information.

2. An ultrasonic medical system according to claim 1, wherein
    the wave transceiver transmits and receives ultrasound with regard to a three dimensional space including the target tissue, and
    each of the first relative coordinate information, the second relative coordinate information, and the combined relative coordinate information is three dimensional relative coordinate information.

3. An ultrasonic medical system according to claim 2, wherein
the second relative coordinate information includes position information and direction information of the wave transceiver using the reference position as an origin.

4. An ultrasonic medical system according to claim 1, further comprising:
a generator which is provided at either one of a measurement origin whose positional relationship with the reference position is known and the wave transceiver, for generating a measurement signal, and
a detector which is provided at the other of the measurement origin and the wave transceiver, for detecting the measurement signal,
wherein the second relative coordinate operation means computes the second relative coordinate information of the wave transceiver using the reference position as an origin, based on the detection result by the detector.

5. An ultrasonic medical system according to claim 4, wherein
the generator is a magnetic field generator for generating a magnetic field, and
the detector is a magnetic field detector for detecting the magnetic field.

6. An ultrasonic medical system according to claim 1, wherein
the first relative coordinate operation means computes the first coordinate information of the target tissue using the wave transceiver as an origin, based on coordinate information specified by an examiner by using an ultrasonic image formed based on the reception wave signal.

7. An ultrasonic medical system according to claim 1, further comprising:
a holder mechanism for holding the wave transceiver; and
a measurement information operation unit for outputting measurement information regarding the wave transceiver which is held by the holder mechanism,
wherein the second relative coordinate operation means computes the second relative coordinate information of the wave transceiver using the reference position as an origin, based on the measurement information.

8. An ultrasonic medical system according to claim 7, wherein
the measurement information is coordinate information of the wave transceiver relative to a measurement origin whose positional relationship with the reference position is known.

9. An ultrasonic medical system according to claim 8, wherein
the holder mechanism is an articulated robot, and
the measurement information is information based on length data and angle data of each movable section of the articulated robot.

10. An ultrasonic medical system according to claim 7, wherein
the wave transceiver is brought into contact with a body surface of a patient, and
the holder mechanism includes a pressure sensor for measuring a contact pressure exerted to the patient by the wave transceiver, for controlling the contact pressure to a predetermined value based on the output from the pressure sensor.

11. An ultrasonic medical system according to claim 1, further comprising a radiation source apparatus for performing irradiation with radiation while controlling an aim based on the combined relative coordinate information.

12. An ultrasonic medical system according to claim 11, wherein
the radiation is a proton beam.

13. An ultrasonic medical system according to claim 11, wherein
the radiation source apparatus controls the aim in accordance with a movement of the target tissue based on the combined relative coordinate information.

14. An ultrasonic medical system according to claim 1, further comprising
a puncture apparatus for controlling a puncture position based on the combined relative coordinate information.

15. A ultrasonic medical system comprising:
an ultrasonic probe which is held by a probe holder mechanism for outputting position and direction information when brought into contact with a body surface of a patient, the ultrasonic probe transmitting/receiving ultrasound with regard to a three dimensional space including a target tissue;
an ultrasonic diagnostic apparatus for obtaining, via the ultrasonic probe, echo data for each of voxels forming the three dimensional space; and
a host controller which extracts a voxel corresponding to the target tissue based on an echo level of the echo data, computes first relative coordinate information of the target tissue using the ultrasonic probe as an origin, computes second relative coordinate information of the ultrasonic probe using a reference position as an origin based on the position and direction information, and computes combined relative coordinate information of the target tissue using the reference position as an origin based on the first relative coordinate information and the second relative coordinate information and outputs the combined relative coordinate information.

16. An ultrasonic medical system according to claim 15, further comprising
a remedial beam source apparatus for performing irradiation with a remedial beam while controlling an aim in accordance with a movement of the target tissue based on the combined relative coordinate information.

* * * * *